United States Patent
Wakamura

(10) Patent No.: US 7,157,503 B2
(45) Date of Patent: *Jan. 2, 2007

(54) ANTIBACTERIAL, ANTIFOULING PAINT FOR CONSTRUCTION MATERIALS AND CONSTRUCTION MATERIALS COATED THEREWITH

(75) Inventor: Masato Wakamura, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 77 days.

This patent is subject to a terminal disclaimer.

(21) Appl. No.: 11/001,143

(22) Filed: Dec. 2, 2004

(65) Prior Publication Data

US 2005/0096408 A1 May 5, 2005

Related U.S. Application Data

(63) Continuation of application No. PCT/JP02/05517, filed on Jun. 4, 2002.

(51) Int. Cl.
*C08K 3/10* (2006.01)
*C08K 3/22* (2006.01)
*C09D 5/16* (2006.01)

(52) U.S. Cl. ............ 523/122; 524/413; 524/414; 524/417; 524/418; 524/421; 428/457

(58) Field of Classification Search ......... 524/497, 524/413, 414, 417, 418, 421; 427/2.24, 2.29, 427/212; 523/122; 428/457
See application file for complete search history.

(56) References Cited

U.S. PATENT DOCUMENTS 5,981,425 A  11/1999  Taoda et al.
6,777,357 B1 *  8/2004  Aso et al. ............. 501/1

FOREIGN PATENT DOCUMENTS

| JP | 11-343210 | 12/1999 |
|---|---|---|
| JP | 2000-1631 | 1/2000 |
| JP | 2000-327315 | 11/2000 |
| JP | 2002-79109 | 3/2002 |

* cited by examiner

*Primary Examiner*—Kriellion Sanders
(74) *Attorney, Agent, or Firm*—Westerman, Hattori, Daniels & Adrian, LLP.

(57) ABSTRACT

An antibacterial, antifouling paint for construction materials contains a coating resin composition and powdery metal-modified apatite. Part of metal atoms in the apatite crystal structure is provided by an optically catalytic metal. Preferably, the metal-modified apatite is a calcium hydroxyapatite which has part of its Ca atoms substituted by Ti.

10 Claims, 4 Drawing Sheets

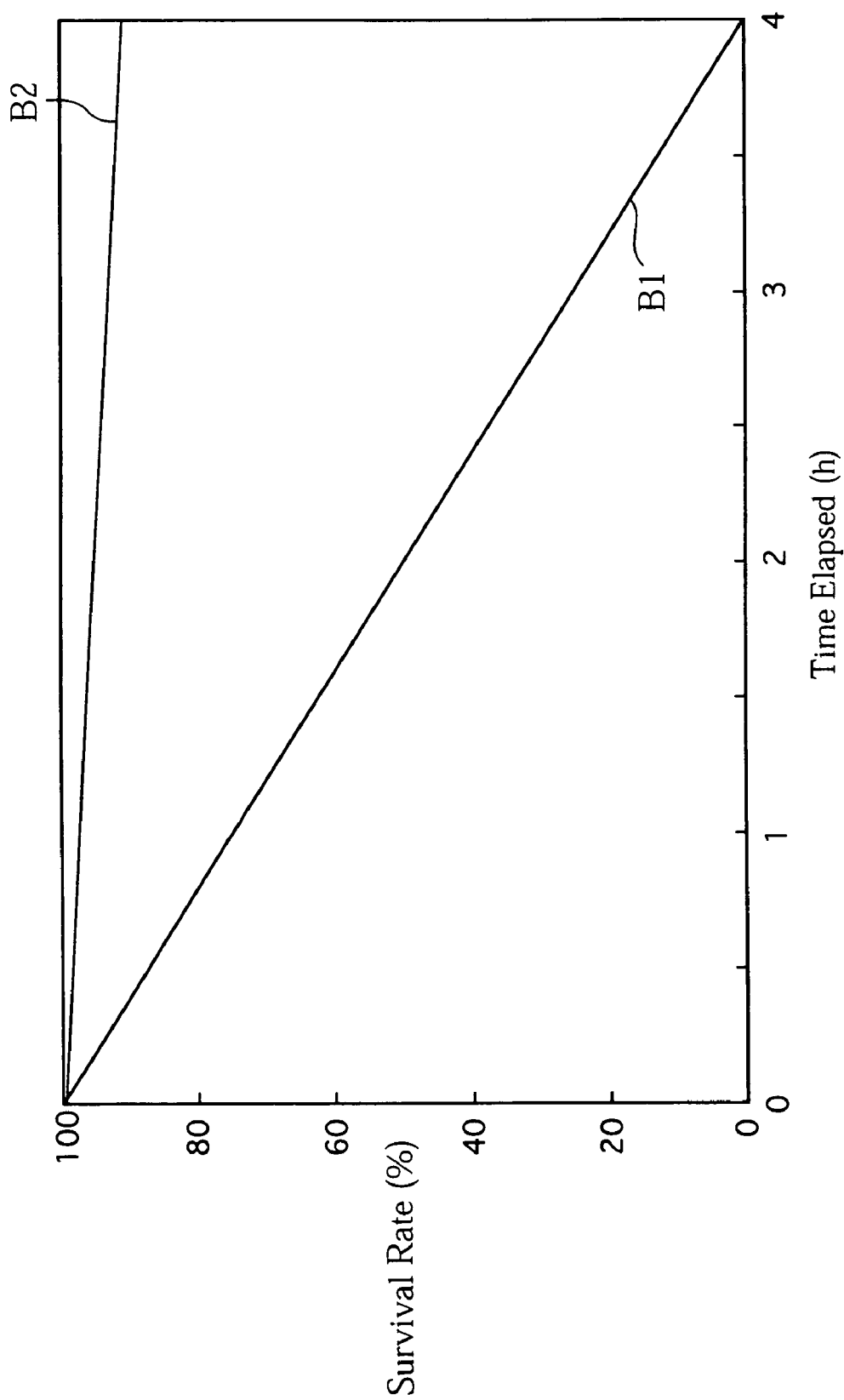

ANTIBACTERIAL, ANTIFOULING PAINT FOR CONSTRUCTION MATERIALS AND CONSTRUCTION MATERIALS COATED THEREWITH

This application is a continuation of international application PCT/JP02/05517 filed on Jun. 4, 2002.

TECHNICAL FIELD

The present invention relates to antibacterial, antifouling paints for coating construction materials which are used to build residences and other buildings. The present invention also relates to construction materials coated with the paint.

BACKGROUND ART

When inside walls and outside walls of residences, other buildings and so on are to be newly coated with paint, conventionally, the old paint on the wall may be scraped off the wall, and then stains such as mold growing in the undercoat is washed off with water before the new paint is applied onto the wall surface. In washing the wall with water, a detergent which contains an antibacterial agent is sometimes used. Such a detergent sterilizes the undercoat surface, so when a coating is made on the undercoat, a certain level of asepticization is achieved between the undercoat surface and the film of paint.

However, according to such a method, the coating is susceptible to contamination such as mold attack from exposed surfaces since the coating is formed to cover the undercoat which is asepticized, and there is no treatment made on the exposed surfaces of the paint coating. Once mold grows on the coating, then coated surface can be stained. Further, once mold grows on the coating, the mold may attack not only the coating but eventually the wall material itself, making the problem worse.

In order to prevent or reduce stains and erosions by microorganisms such as mold, there is a method which is already public, of rendering antibacterial capability to inner walls and outer walls of buildings by coating the walls with a paint which contains a powdery optical catalyst. The optical catalyst can be provided by titanium oxide ($TiO_2$) or other semiconductor materials which work as optical catalyst.

Generally, in the semiconductor materials which work as optical catalyst, absorption of a light which has a level of energy equivalent to a band gap between the valence band and the conduction band causes transition of electrons from the valence band to the conduction band. Due to this transition of electrons, the valence band has electron holes. The electrons in the conduction band move to a matter adsorbed on the surface of the optically catalytic semiconductor, and this movement can chemically reduce the adsorbed matter. The electron holes in the valence band get electrons from the matter which is adsorbed on the surface of the optically catalytic semiconductor, and this behavior can oxidize the adsorbed matter.

In titanium oxide ($TiO_2$) which has the optical catalyst capability, the electrons which have moved to the conduction band reduce oxygen in the air, to produce supueroxide anion ($.O_2^-$). At the same time, the electron holes in the valence band oxidize water which is adsorbed on the surface of titanium oxide, to produce hydroxy radicals ($.OH$). Hydroxy radials are highly oxidative. Therefore, if the material which is adsorbed by the optical catalytic titanium oxide is an organic matter for instance, working of the hydroxy radicals may eventually decompose the organic matter into water and carbon dioxide. Among many semiconductor materials which have an optical catalyst capability, titanium oxide in particular works as a superior catalyst in such an oxidation-decomposition reaction as the above, and therefore is used widely in antibacterial agent, deodorants, environmental purification agents, and so on.

A problem, however, is that the titanium oxide optical catalyst itself can only work as a catalyst by absorbing light. For this reason, even if a wall material is coated with a paint which contains titanium oxide that has the optical catalyst capability, antibacterial or antifouling effect based on the optically catalytic decomposition cannot be expected if the wall material is used in a dark place in the building or stored at a dark place where titanium oxide can absorb no or little light. Further, even if the wall material is used at a sunny place, titanium oxide cannot absorb light or enough amount of light during the night time, and so antibacterial effect based on the optical catalyst capability cannot be expected, either.

Further, titanium oxide itself does not have a strong capability to adsorb matters on its surfaces. Therefore, in order to make titanium oxide exhibit its catalytic capability sufficiently, it is necessary to improve contact efficiency between titanium oxide and the target matter which is to be oxidized and decomposed. JP-A 11-343210 and JP-A 2000-1631 for example, disclose techniques for coexistence of titanium oxide and an adsorbent matter in a paint, with an object of improved contact between titanium oxide and the target matter to decompose.

An adsorbent matter known in such an application is calcium hydroxyapatite (Ca HAP). Ca HAP can exchange ions with both cations and anions, and therefore is highly adsorbent. In particular, it is superb in adsorbing organic matters such as protein. For this reason, Ca HAP has been a subject of research in applied technology in many different fields including chromatography adsorbent, chemical sensor, and ion exchanger. However, adding an adsorbent matter such as Ca HAP and titanium oxide separately to a paint and dispersing each of the matters sufficiently is not efficient in manufacture of the paint. Further, making titanium oxide and an adsorbent matter simply coexist in a paint can only make small improvement in contact efficiency between titanium oxide and target matters to decompose.

DISCLOSURE OF THE INVENTION

The present invention was made under these circumstances, and it is therefore an object of the present invention to provide an antibacterial, antifouling paint for coating construction materials which exhibit good antibacterial effects both in well-lighted and dark places. Another object is to provide construction materials coated with the paint.

A first aspect of the present invention provides an antibacterial, antifouling paint for construction materials. This antibacterial, antifouling paint includes a coating resin composition and powdery metal-modified apatite which has part of metal atoms in its apatite crystal structure provided by an optically catalytic metal.

A second aspect of the present invention provides a construction material. This construction material is coated with an antibacterial, antifouling paint which includes a coating resin composition and powdery metal-modified apatite which has part of metal atoms in its apatite crystal structure provided by an optically catalytic metal.

In the first and the second aspects of the present invention, preferably, the metal-modified apatite is a calcium hydroxyapatite which has part of its Ca atoms substituted by Ti.

Preferably, Ti/(Ti+Ca) in the metal-modified apatite has a value of 0.03–0.11 (molar ratio).

Preferably, the metal-modified apatite is sintered at 580–660° C. after formation.

Preferably, the antibacterial, antifouling paint contains the metal-modified apatite at a proportion of 0.01–30 wt %.

BRIEF DESCRIPTION OF THE DRAWINGS

FIG. 4 is a graph showing antibacterial effect in Comparative Example 1 and Comparative Example 2.

BEST MODE FOR CARRYING OUT THE INVENTION

Figure 1:
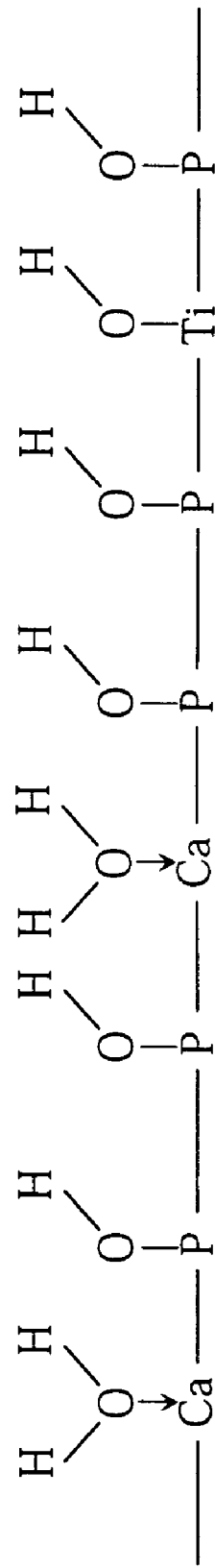
FIG. 1 shows a surface chemical structure model of a metal-modified apatite used in the present invention.

An antibacterial, antifouling paint according to the present invention contains a coating resin composition, and powder of metal-modified apatite which has an optical catalyst capability. The metal-modified apatite powder is dispersed in the coating resin composition.

Examples of the coating resin composition used in the present invention include, polymers containing silicon, polymers containing fluorine, epoxy resins, urethane resins, saturated polyester resins, unsaturated polyester resins, melamine resins, phenol resins, polyamide resins, ketone resins, acrylic resins, vinyl resins, and hydrocarbon resins.

The metal-modified apatite used in the present invention is a complex compound, at the atomic level, of so called apatite which is rich in adsorbing capability and a metal oxide which has an optical catalyst capability.

In the metal-modified apatite, the apatite which provides the basic structure can be expressed in the following general formula:

$$A_x(BO_y)_z X_s \quad (1)$$

In the formula (1), the symbol A represents a metal atom such as Ca, Co, Ni, Cu, Al, La, Cr, Fe and Mg. The symbol B represents such an atom as P and S. The symbol X represents a hydroxyl (—OH), a halogen atom (e.g. F and Cl), and so on. More specifically, the apatite can be provided by a metal salt of hydroxyapatite, fluoroapatite and chloroapatite, as well as tricalcium phosphate and calcium hydrogen phosphate and so on. Preferably, the apatite which provides the basic structure of the metal-modified apatite used in the present invention is a hydroxyapatite which is expressed in the above formula, with the symbol X provided by hydroxyl (—OH). More preferably, it is a calcium hydroxyapatite (Ca HAP), with the symbol A in the above formula provided by Calcium (Ca), the symbol B provided by phosphorus (P), and the symbol x provided by hydroxyl (—OH), i.e. $Ca_{10}(PO_4)_6(OH)_2$.

The metal-modified apatite according to the present invention is an apatite which is expressed by the above formula (1), and in which part of the metal atoms A in the apatite crystal structure is substituted by atoms of an optical catalytic metal. Here, the term optical catalytic metal refers to metals which are capable of serving as an optical catalyst center in the form of oxide. The optical catalytic metal can be provided by e.g. titanium (Ti), zinc (Zn), tungsten (W), manganese (Mn), tin (Ti), indium (In) and iron (Fe). When atoms of such an optical catalytic metal are taken into the apatite crystal structure as part of the metal atoms providing the crystal structure of the apatite expressed in the formula (1), there is formed an optical catalytic partial structure within the apatite crystal structure which has an optical catalyst capability. The optical catalytic partial structure is, more specifically, thought to be built with the atoms of the optical catalytic metal which are taken into the apatite crystal structure in place of the metal atoms A in the formula (1) and oxygen atoms in the formula (1), having an equivalent structure to a metal oxide which has an optical catalyst capability. It is presumed that formation of such an optical catalytic partial structure as the above gives the apatite crystal an optical catalyst capability as a property of the apatite crystal.

FIG. 1 shows a surface chemical structure model of Ti—Ca HAP, with the optically catalytic metal provided by Ti and the hydroxyapatite provided by calcium hydroxyapatite.

As shown in FIG. 1, in the Ti—Ca HAP, inclusion of Ti provides an optical catalytic partial structure around Ti within the apatite crystal structure. Structures other than the optical catalytic partial structure are considered to have the same adsorbing capability as of a normal Ca HAP. In such a Ti—Ca HAP, optical catalyst sites which have the optical catalytic partial structure and adsorbing sites which have a high capability to absorb a predetermined organic matter (not illustrated) or a target matter to decompose scatter on the same crystal plane at an atomic scale. Therefore, the Ti—Ca HAP has both of a high adsorbing capability and an optical catalyst capability, being able to exhibit antibacterial and antifouling capabilities efficiently.

Specifically, under the presence of light, the titanium-oxide-like optical catalyst sites in the Ti—Ca HAP behave like titanium oxide, producing hydroxy radicals (.OH) from adsorbed water, whereas the adsorbing sites adsorb the organic matter. The adsorbed organic matter moves on the surface of Ti—Ca HAP due to surface diffusion, to or near the optical catalyst sites, where it is oxidized and decomposed by the hydroxy radicals. Also, as the adsorbing sites of the Ti—Ca HAP adsorb microorganisms powerfully, growth of the microorganisms is prevented or suppressed. Therefore, even if the Ti—Ca HAP is not in a well-lighted environment and the optical catalyst sites do not work as the optical catalyst, the Ti—Ca HAP still provides antibacterial capability.

The metal-modified apatite should preferably contain the optically catalytic metal at a rate of 3–11 mol % with respect to a total metal content in its apatite crystal structure, in view of efficient improvement both in the adsorption by the metal-modified apatite and in the optical catalyst capability. Specifically, in Ti—Ca HAP for example, Ti/(Ti+Ca) should preferably have a value 0.03–0.11 (molar ratio). If the ratio is greater than 11 mol %, the crystal structure maybe distorted, resulting in decreased catalyst capability. If the ratio is smaller than 3 mol %, there is an excess of the adsorbing sites, and too much of the adsorbed matter may not be processed sufficiently at too few optical catalyst sites. Both of these are not preferable in view of catalyst efficiency.

By coating construction materials with the antibacterial, antifouling paint according to the present invention which contains such a metal-modified apatite as described above, it becomes possible to give the construction materials a superb antibacterial and antifouling capabilities.

The metal-modified apatite powder which is contained in the antibacterial, antifouling paint according to the present invention exhibits a decomposing capability which is based on the optical catalyst capability in well-lighted environments. For this reason, if organic matters such as mold attach to the construction material which is coated with the antibacterial, antifouling paint according to the present invention, the organic matters are killed in the well-lighted environment because their cell membranes and other parts are decomposed. Metabolites of the organic matters are also decomposed. With these, stains on the construction materials due to the growth of microorganisms such as mold and their metabolites are eliminated or reduced sufficiently. In other words, the construction materials are rendered antibacterial and antifouling. Through such an antibacterial and antifouling functions in the well-lighted environment, the construction materials are protected from deterioration.

Further, the metal-modified apatite powder which is contained in the antibacterial, antifouling paint according to the present invention exhibits an antibacterial capability, as described above which is based on the adsorbing capability, in dark environments. For this reason, if organic matters such as mold attach to the construction material which is coated with the antibacterial, antifouling paint according to the present invention, growth of the organic matters is prevented or suppressed. With this, stains on the construction materials due to growth of microorganisms such as mold are eliminated or reduced sufficiently. In other words, the construction materials are rendered antibacterial. Through such an antibacterial function in dark environments, the construction materials are protected from deterioration. The microorganisms whose growth has been prevented or suppressed in the dark environment are decomposed once the construction material is brought in a well-lighted environment.

As described, the antibacterial, antifouling paint according to the present invention is capable of working not only under presence of light but also under absence of light, and as a result, exhibits superb antibacterial, antifouling effects. Therefore, by applying the antibacterial, antifouling paint according to the present invention to wall materials and other construction materials, it is possible to suppress deterioration of the construction materials sufficiently.

Figure 2:
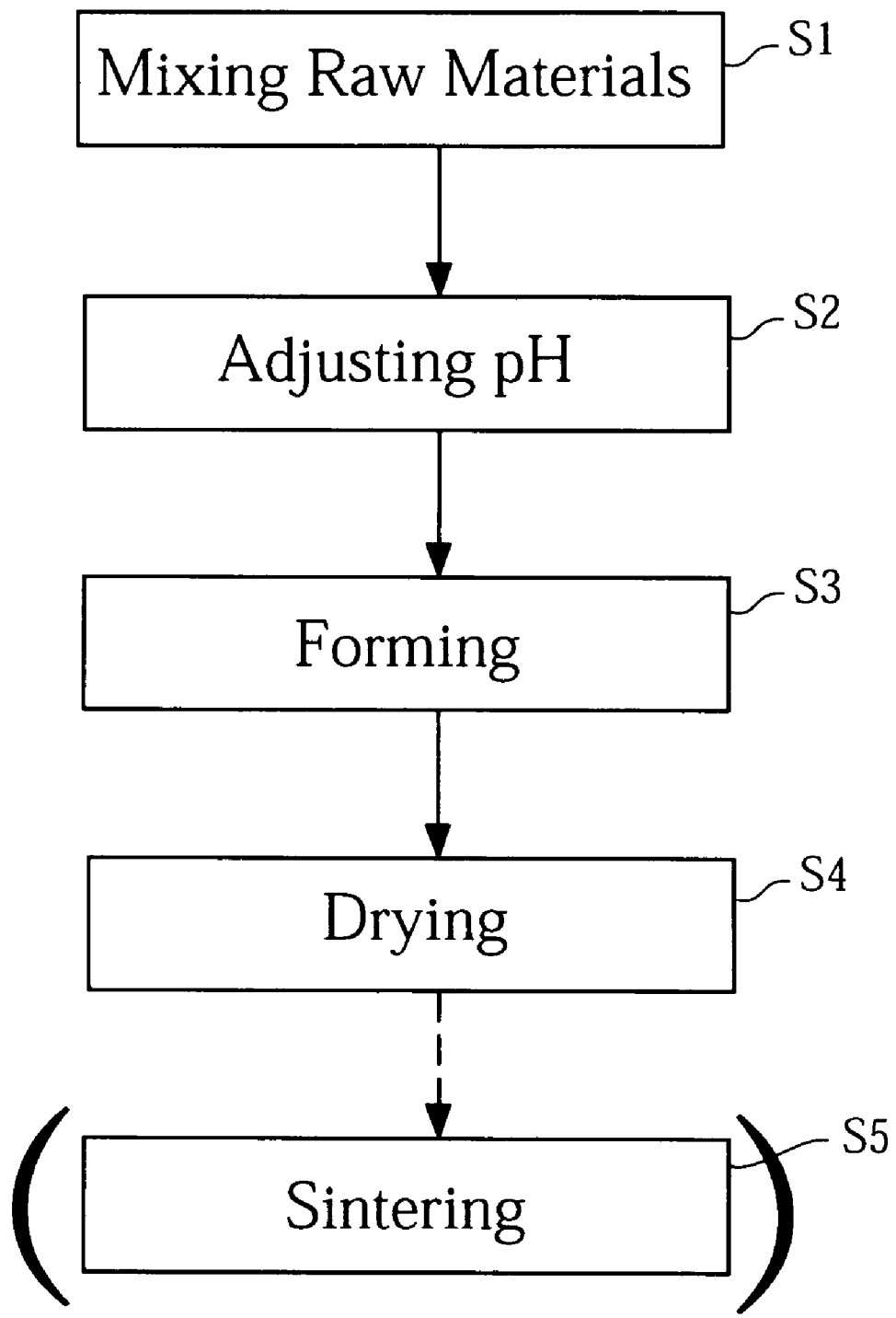
FIG. 2 is a flowchart of a method of fabrication of the metal-modified apatite used in the present invention.

FIG. 2 is a flowchart of a fabrication of the metal-modified apatite used in the present invention. In the fabrication of the metal-modified apatite, first, in a raw material mixing step S1, raw materials for forming the metal-modified apatite are mixed. For example, chemical species representing the symbols A, $BO_3$, and X in the apatite general formula described earlier are added to a single aqueous solution, by respective predetermined amounts, and then mixed. If the metal-modified apatite which is supposed to be formed is Ti—Ca HAP, calcium nitrate for example can be used as a Ca supplier. Phosphoric acid for example can be a $PO_4$ supplier. Hydroxyls are supplied from aqueous solution of alkalis such as aqueous solution of ammonia, aqueous solution of calcium hydroxide or sodium hydroxide, which will be used in a step of pH adjustment to be described later. The optically catalytic metal or Ti can be supplied from titanium chloride or titanium sulfide.

The rate of the optically catalytic metal to a total metal content in the apatite crystal structure should preferably be in the range of 3–11 mol % as mentioned earlier. Therefore, in the material mixing step S1, it is preferable that the supply amount is determined for each of the raw materials, and adjustments are made to relative physical quantities to be supplied, so that the rate of the optical catalytic metal to a total metal content in the apatite crystal structure will become 3–11 mol %.

Next, in a pH adjustment step S2, the raw material solution which has been prepared as the above is adjusted to a specific pH at which formation of the target metal-modified apatite commences. The pH adjustment can be made by using aqueous solution of ammonia, aqueous solution of calcium hydroxide, aqueous solution of sodium hydroxide and so on. When forming e.g. Ti—Ca HAP as the metal-modified apatite, the raw material solution should preferably be adjusted to a value in a range of pH 8–10.

Next, in a formation step S3, formation of the metal-modified apatite is promoted, whereby crystallization of the target metal-modified apatite is promoted. Specifically, for example, after coprecipitating the apatite components and part of the optically catalytic metal in the raw material solution, the solution is aged at 100° C. for six hours, to obtain highly crystallized optical catalytic metal. When manufacturing Ti—Ca HAP for example, the coprecipitation process in this step allows Ti ions to be taken into Ca positions in the apatite crystal structure, allowing Ti—Ca HAP to grow.

Next, in a drying step S4, the metal-modified apatite which has been formed in the previous step is dried. Specifically, the powder of metal-modified apatite which has been separated in the formation step S3 is filtered, and then the sediment which has been filtered out is cleaned in pure water, and then dried. The drying temperature should preferably be 100–200° C. This step removes liquid components in the raw material solution from the metal-modified apatite.

The powdery metal-modified apatite thus fabricated undergoes a sintering step S5 as necessary. In the sintering step S5, the metal-modified apatite is heated again, separately from heating in the drying step S4, whereby the metal-modified apatite is sintered. The sintering temperature should preferably be 580–660° C. In the case of Ti—Ca HAP for example, this sintering step improves optical catalyst activity.

When preparing the antibacterial, antifouling paint according to the present invention, the powdery metal-modified apatite which is manufactured in this way is added to a coating resin composition and these components are mixed together. The addition is made so that the metal-modified apatite content in the antibacterial, antifouling paint becomes 0.01–30 wt %. If the content is smaller than 0.01 wt %, it tends to be impossible to achieve a sufficient antibacterial effect required of construction materials. If the content is greater than 30 wt %, the metal-modified apatite tends to coagulate excessively in the paint, making it difficult to dissipate the metal-modified apatite appropriately, and if such a paint is applied to construction materials, surface texture of the construction materials is deteriorated sometimes.

When adding, the metal-modified apatite powder maybe added directly to the coating resin composition, or the metal-modified apatite powder may first be dissipated in an appropriate diluent such as water and then mixed with the coating resin composition.

In order to achieve good dispersion of the metal-modified apatite in the paint, metal-modified apatite powder should, for example, be pulverized before it is added to the coating resin composition. The pulverization can be made by first dispersing the metal-modified apatite powder in a dispersion medium such as water, and then pulverizing the metal-modified apatite powder in the medium, using a ball mill.

The medium may be any diluent or thinner compatible with the coating resin composition. Such a pulverization process appropriately breaks up relatively large secondary grains of the metal-modified apatite which are coagulated grains made up of smaller primary grains. If the metal-modified apatite is pulverized in such a way, then added to the coating resin composition together with the medium, and then mixed together, it becomes possible to disperse the metal-modified apatite, which has appropriate sizes as the secondary grain, in the coating resin composition. As a result, it becomes possible to appropriately avoid deterioration in the texture of painted surface which can otherwise be caused by coagulation of the metal-modified apatite powder.

The antibacterial, antifouling paint thus prepared can be sprayed for example, onto outer walls, inner walls, poles and other construction materials. The film of paint formed on the surface of construction materials works on microorganisms and so on not only in the well-lighted environments but also in dark environments as has been described, and exhibits antibacterial and antifouling effects. As a result, it becomes possible to appropriately avoid contamination and deterioration of the construction materials.

Next, examples of the present invention will be described together with comparative examples.

EXAMPLE 1

<Manufacture of a Metal-Modified Apatite>

In the present Example, Ti—Ca HAP was made as the metal-modified apatite. Specifically, a liter of decarbonated pure water was prepared. To this pure water, calcium nitrate, titanium sulfide and phosphoric acid were added and mixed in nitrogen atmosphere. The concentration of calcium nitrate was adjusted to 0.09 mol/L, the concentration of titanium sulfite was adjusted to 0.01 mol/L whereas the concentration of phosphorus acid was adjusted to 0.06 mol/L. Next, the pH of the raw material solution was adjusted to 9.0 by adding ammonia water of the 15 mol/L concentration. Next, the raw material solution was aged at 100° C. for six hours. Through these operations, the metal-modified apatite occurred and precipitated in the raw material solution, and the raw material solution became a suspension. The suspension was filtered, and the separated deposit was cleaned with five liters of pure water, and then dried in a dry oven at 70° C. for 12 hours, to obtain Ti—Ca HAP which has an average size of 0.05 μm per grain. This Ti—Ca HAP had an abundance ratio between Ti and Ca, which was Ti:Ca=1:9. In other words, the abundance ratio of Ti, which serves as the catalyst metal atoms, to a total amount of metal atoms contained in the metal-modified apatite crystal structure was 10 mol %. The abundance ratio of Ti to Ca was determined on the basis of quantitative analysis using ICP-AES (Plasma Emission Spectrometry).

<Preparation of an Antibacterial, Antifouling Paint>

The Ti—Ca HAP powder obtained as the above was mixed with a silicone paint for residential outside walls (Brand name: Ales Silicon, manufactured by Kansai Paint Co., Ltd.) at a weight ratio of 10:90, and the Ti—Ca HAP was uniformly dispersed in the paint, to obtain an antibacterial, antifouling paint according to the present invention.

<Antibacterial Test>

The antibacterial, antifouling paint prepared as the above was subjected to an antibacterial antifouling test. Specifically, first, the antibacterial, antifouling paint was applied, by means of spin coating, on a glass plate which had a size of 50 mm×50 mm. Next, the paint was dried to form an antibacterial, antifouling coating on the glass plate. Next, a drop of E. coli bacteria culture was dropped on the antibacterial, antifouling coating. The coating was left at 25° C. under ultraviolet radiation (<300 nm). Living population of the E. coli bacteria was counted a plurality of times at a predetermined time interval measured from the beginning of ultraviolet radiation, and survival rate with respect to the original living population was calculated for each count. Results were plotted in a graph A1 in FIG. 3, with the horizontal axis representing time and the vertical axis representing the survival rate.

EXAMPLE 2

The same antibacterial, antifouling paint as in Example 1 was used, and the same method as in Example 1 was employed to form an antibacterial, antifouling coating on a glass plate which had a size of 50 mm×50 mm. Further, the same operation and counting methods as in Example 1 were applied, except that no ultraviolet radiation was made to the E. coli bacteria and the antibacterial, antifouling paint was kept in a dark place. Results were plotted in a graph A2 in FIG. 3, with the horizontal axis representing time and the vertical axis representing the survival rate of the E. coli bacteria.

EXAMPLE 3

The same Ti—Ca HAP powder as used in Example 1 was further sintered at 650° C. for 30 minutes. Then, using this Ti—Ca HAP powder, the same steps were followed to prepare an antibacterial, antifouling paint. Next, using this antibacterial, antifouling paint, the same method as in Example 1 was employed to form an antibacterial, antifouling coating on a glass plate which had a size of 50 mm×50 mm. Then, the same operation and counting methods as in Example 1 were applied. Results were plotted in a graph A3 in FIG. 3, with the horizontal axis representing time and the vertical axis representing the survival rate of the E. coli bacteria.

EXAMPLE 4

The same Ti—Ca HAP powder as in Example 3 was used and the same method as in Example 1 was employed to form an antibacterial, antifouling paint on a glass plate which had a size of 50 mm×50 mm. Further, the same operation and counting methods as in Example 1 were applied, except that no ultraviolet radiation was made to the E. coli bacteria and the antibacterial, antifouling paint was kept in a dark place. Results were plotted in a graph A4 in FIG. 3, with the horizontal axis representing time and the vertical axis representing the survival rate of the E. coli bacteria.

COMPARATIVE EXAMPLE 1

Optically catalytic titanium oxide powder (Brand name: ST21, manufactured by Ishihara Sangyo Kaisha Ltd.) was mixed with a silicone paint for residential outside walls (Brand name: Ales Silicon, manufactured by Kansai Paint Co., Ltd.) at a weight ratio of 10:90, and the optically catalytic titanium oxide powder was uniformly dispersed in the paint, to obtain a paint according to Comparative Example 1. The paint thus prepared was subjected to an antibacterial antifouling test. Specifically, first, the paint was applied by means of spin coating on a glass plate which had a size of 50 mm×50 mm. Next, the paint was dried to form a film of coating on the glass plate. Next, a drop of E. coli bacteria culture was dropped on the antibacterial, antifouling paint. The paint was left at 25° C. under ultraviolet radiation (<300 nm). Living population of the *E. coli* bacteria was counted a plurality of times at a predetermined time interval measured from the beginning of ultraviolet radiation, and survival rate with respect to the original living population was calculated for each counting. Results were plotted in a graph B1 in FIG. 4, with the horizontal axis representing time and the vertical axis representing the survival rate.

COMPARATIVE EXAMPLE 2

The same paint as in Comparative Example 1 was used, and the same method as in Comparative Example 1 was employed to form a coating on a glass plate which had a size of 50 mm×50 mm. Further, the same operation and counting methods as in Comparative Example 1 were applied, except that no ultraviolet radiation was made to the *E. coli* bacteria and the paint was kept in a dark place. Results were plotted in a graph B2 in FIG. 4, with the horizontal axis representing time and the vertical axis representing the survival rate of the *E. coli* bacteria.

[Evaluation on Antibacterial Effect]

Figure 3:
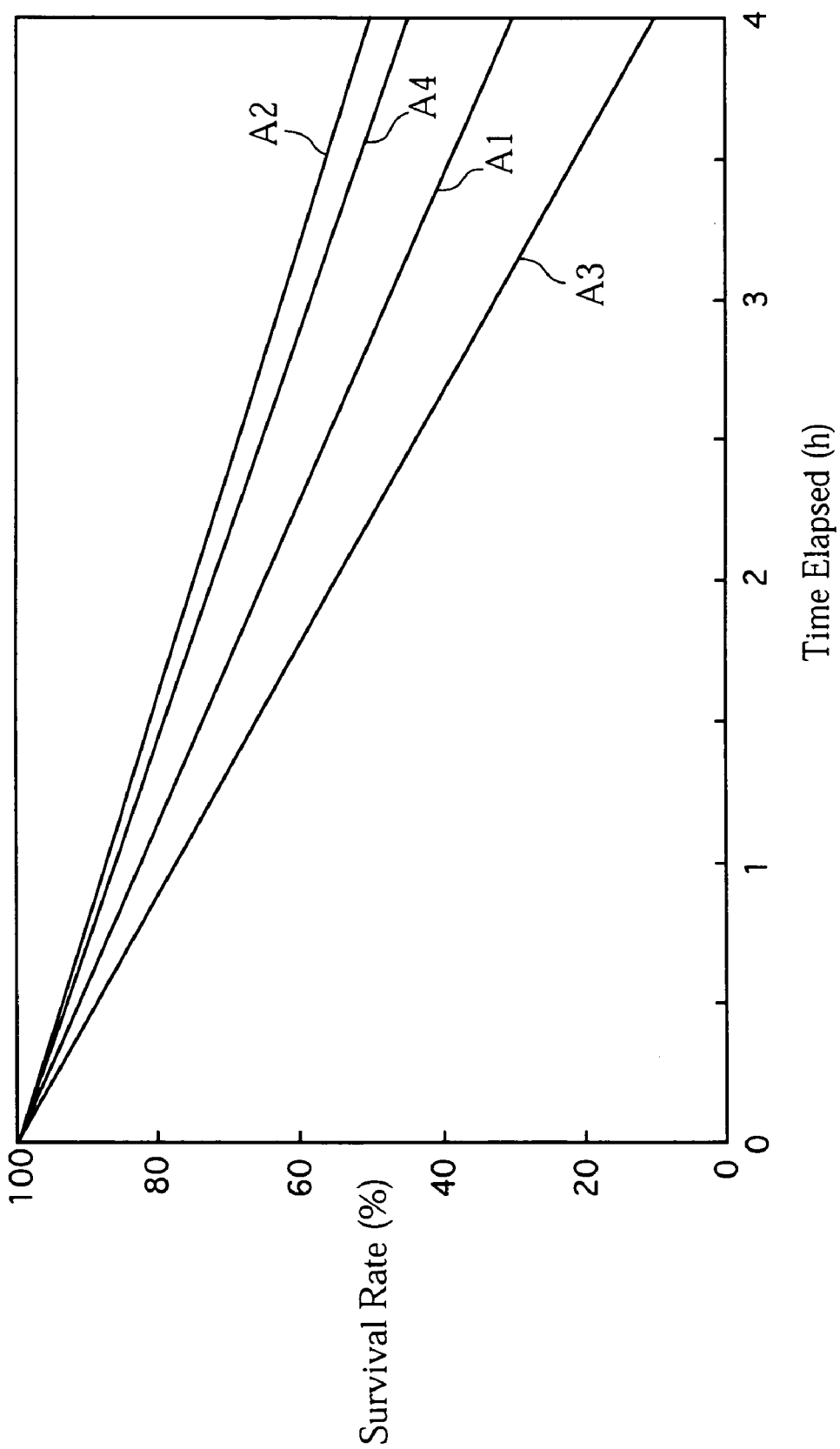
FIG. 3 is a graph showing antibacterial effect in Example 1 through Example 4.

As shown in FIG. 3 and FIG. 4, the survival rate of *E. coli* bacteria in four hours since each sample was left in respective environments was; 30% in Example 1, 50% in Example 2, 10% in Example 3, 45% in Example 4, 0% in Comparative Example 1 and 90% in Comparative Example 2. From this result, it will be easy to understand that a good antibacterial effect can be obtained both under a well-lighted environment and under a dark environment in Examples 1 through 4 in which antibacterial, antifouling paints according to the present invention were used. This is because the film formed of the antibacterial, antifouling paint according to the present invention is capable of exhibiting antibacterial action based on combined effect of a high level of adsorbing capability and decomposing capability by the optical catalyst in well-lighted environments while in dark environments, it is capable of exhibiting antibacterial action based on the high level of adsorbing capability. Also, it will be easy to understand that even better antibacterial effect can be obtained from Examples 3 and 4 which used a sintered metal-modified apatite than from Examples 1 and 2 which used a non-sintered metal-modified apatite. This is attributable to the sintering process which is believed to improve crystallization and optical catalytic activity of the metal-modified apatite, leading to improved antibacterial action.

On the other hand, in the Comparative Examples 1 and 2 which used a paint containing titanium oxide in place of the metal-modified apatite, it will be easy to understand that there is little antibacterial effect under the environment without light (ultraviolet ray). This is because titanium oxide works only as an optical catalyst which is energized by normal light and cannot work at a dark place.

The invention claimed is:

1. An antibacterial, antifouling paint for construction materials, comprising:
   a coating resin composition; and
   powdery metal-modified apatite having part of metal atoms in its apatite crystal structure provided by an optically catalytic metal.

2. The antibacterial, antifouling paint according to claim 1, wherein the metal-modified apatite is a calcium hydroxyapatite having part of its Ca substituted with Ti.

3. The antibacterial, antifouling paint according to claim 2, wherein Ti/(Ti+Ca) in the metal-modified apatite has a value of 0.03–0.11 (molar ratio).

4. The antibacterial, antifouling paint according to claim 1, wherein the metal-modified apatite is sintered at 580–660° C. after formation.

5. The antibacterial, antifouling paint according to claim 1, wherein the metal-modified apatite is contained at a proportion of 0.01–30 wt %.

6. A construction material coated with an antibacterial, antifouling paint, the paint comprising a coating resin composition and powdery metal-modified apatite having part of metal atoms in its apatite crystal structure provided by an optically catalytic metal.

7. The construction material according to claim 6, wherein the metal-modified apatite is a calcium hydroxyapatite having part of its Ca atoms substituted by Ti.

8. The construction material according to claim 7, wherein Ti/(Ti+Ca) in the metal-modified apatite has a value 0.03–0.11 (molar ratio).

9. The construction material according to claim 6, wherein the metal-modified apatite is sintered at 580–660° C. after formation.

10. The construction material according to claim 6, wherein the metal-modified apatite is contained at a proportion of 0.01–30 wt %.

* * * * *